United States Patent
Doring et al.

(10) Patent No.: US 9,517,195 B2
(45) Date of Patent: Dec. 13, 2016

(54) COSMETIC COMPOUNDS HAVING TIME-DELAYED ACTIVE INGREDIENT RELEASE

(71) Applicant: Henkel AG & Co. KGaA, Duesseldorf (DE)

(72) Inventors: Thomas Doring, Dormagen (DE); Natascha Schevardo, Erkrath (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/621,446

(22) Filed: Feb. 13, 2015

(65) Prior Publication Data

US 2015/0157552 A1 Jun. 11, 2015

Related U.S. Application Data

(63) Continuation of application No. PCT/EP2013/065813, filed on Jul. 26, 2013.

(30) Foreign Application Priority Data

Aug. 17, 2012 (DE) .................. 10 2012 214 662

(51) Int. Cl.

| A61K 8/37 | (2006.01) |
|---|---|
| A61K 8/73 | (2006.01) |
| A61K 8/92 | (2006.01) |
| A61K 8/02 | (2006.01) |
| A61K 8/81 | (2006.01) |
| A61Q 15/00 | (2006.01) |
| A61Q 13/00 | (2006.01) |
| A61K 8/11 | (2006.01) |

(52) U.S. Cl.
CPC . *A61K 8/92* (2013.01); *A61K 8/11* (2013.01); *A61K 8/37* (2013.01); *A61K 8/73* (2013.01); *A61K 8/731* (2013.01); *A61K 8/8111* (2013.01); *A61Q 13/00* (2013.01); *A61Q 15/00* (2013.01); *A61K 2800/244* (2013.01); *A61K 2800/56* (2013.01)

(58) Field of Classification Search
None
See application file for complete search history.

(56) References Cited

U.S. PATENT DOCUMENTS

| 4,152,272 A | 5/1979 | Young |
| 4,731,243 A | 3/1988 | Lindauer et al. |
| 7,053,034 B2 * | 5/2006 | Shefer ............. A61Q 13/00 510/101 |
| 2005/0031565 A1 | 2/2005 | Prud'Homme et al. |
| 2008/0181858 A1 * | 7/2008 | Davis .............. A61K 8/73 424/59 |
| 2010/0036066 A1 * | 2/2010 | Fujimura .......... C08F 10/14 526/126 |
| 2012/0034017 A1 * | 2/2012 | Archer ............. A61K 8/06 401/214 |

FOREIGN PATENT DOCUMENTS

| DE | 2731318 A1 | 2/1979 |
| EP | 0397245 A2 | 11/1990 |
| EP | 0908174 A2 | 4/1999 |
| EP | 1584330 A1 | 10/2005 |
| WO | 02/060399 A1 | 8/2002 |
| WO | 2004/084844 A2 | 10/2004 |

OTHER PUBLICATIONS

PCT International Search Report (PCT/EP2013/065813) dated May 19, 2014.
Kirk-Othmer, "Encyclopedia of Chemical Technology", Third Edition, vol. 8, pp. 913-916, 1979.

* cited by examiner

*Primary Examiner* — Abigail Fisher
(74) *Attorney, Agent, or Firm* — P. Scott Smith

(57) ABSTRACT

The invention relates to particles including, relative in each case to the particle weight, 30 to 90 wt. % of polyalphaolefin wax(es) and 10 to 70 wt. % of one or more cosmetic active agents, selected from fragrances, cooling active agents and mixtures of fragrances and cooling active agents, as well as to cosmetic compositions containing water and 0.01 to 10 wt. %, relative to the weight of the cosmetic composition, of one or more of the aforementioned particles.

15 Claims, No Drawings

COSMETIC COMPOUNDS HAVING TIME-DELAYED ACTIVE INGREDIENT RELEASE

FIELD OF THE INVENTION

The present invention generally relates to particles consisting of a selected wax material and a fragrance or cooling active agent as well as to hydrous cosmetic compositions, in particular antiperspirant compositions and deodorant compositions, containing these particles. The wax particles serve as time-delay carriers, from which under the influence of heat from the skin the fragrances or cooling active agents they contain are gradually released.

BACKGROUND OF THE INVENTION

There are numerous possibilities for applying sweat-inhibiting compositions to the skin. Dimensionally stable stick compositions are stroked over the skin from a stick dispenser until an effective amount has been applied. Gels and creams too can be applied from stick-like dispensers, which are stroked with a dispenser surface over the skin. For sweat-inhibiting and/or deodorizing compositions for the armpit region in particular, numerous different application forms have been developed: above all, in addition to those already mentioned, propellant-containing and propellant-free sprays and roll-on compositions. In the latter case an easily thickened liquid is applied from a storage container via a rotatably mounted ball by rolling it over the skin. Sweat-inhibiting roll-on compositions can be anhydrous and oil-based; for example, the oil-based decoction of conventional antiperspirant sprays is also suitable for presentation in roll-on form. Here the sweat-inhibiting active agent takes the form of a suspended powder in an oil, which is thickened with a lipophilic gelling agent to prevent the powder particles from settling. Such roll-ons have virtually no market presence, however. Conventional sweat-inhibiting roll-on compositions are water-based, in other words their water content is approximately 50 wt. % or more of their total weight. The antiperspirant active agent, usually a sweat-inhibiting aluminum or aluminum zirconium compound, is in dissolved form. Thickening is necessary here to enable the composition to be applied with a roll-on applicator.

The use of certain thickening agents can lead to the scent impression of the agents being perceived as inhomogeneous. Often the scent impression immediately after application is very strong and is sometimes felt to be intrusive, whereas a few hours after application the scent impression is often perceived as being too weak.

A further disadvantage of known antiperspirant roll-ons in emulsion form is their inadequate temperature stability. In the event of sharp temperature variations, for example, to which the products can be exposed during transportation and storage, this can cause the droplets of the dispersed phase to coalesce, adversely affecting the product properties. This also affects scents.

A problem addressed by the present application was therefore that of providing water-based antiperspirant roll-ons having improved long-term stability, in particular an improved long-term scent effect.

A further problem addressed by the present application was that of providing antiperspirant roll-ons in the form of hydrous emulsions having improved temperature stability.

Surprisingly it was found that the use of polyalphaolefin waxes prepares certain active agents, in particular scents, in such a way that a clear improvement in the temperature and scent stability and a markedly improved long-term scent effect is achieved.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

A particle containing, relative in each case to the particle weight, 30 to 90 wt. % of polyalphaolefin wax(es) and 10 to 70 wt. % of one or more cosmetic active agents, selected from fragrances, cooling active agents and mixtures of fragrances and cooling active agents.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present application provides a particle containing, relative in each case to the particle weight, 30 to 90 wt. % of polyalphaolefin wax(es) and 10 to 70 wt. % of one or more cosmetic active agents, selected from fragrances, cooling active agents and mixtures of fragrances and cooling active agents.

The particles according to the invention contain, relative to their weight, 30 to 90 wt. % of at least one polyalphaolefin wax. Preferred particles according to the invention contain 35 to 85 wt. %, more preferred particles 40 to 80 wt. %, still more preferred particles 45 to 77.5 wt. % and particles that are preferred in particular 50 to 75 wt. % of polyalphaolefin wax(es).

Polyalphaolefin waxes are known per se and can be obtained for example by polymerization of alpha-olefins. Particularly suitable poly-α-olefins according to the invention can be obtained by the dehydrating polymerization of primary alcohols in the presence of acid aluminum phyllosilicates at a temperature in the range from 60 to 340° C. The primary alcohol here is preferably selected from the group of
a) unsaturated monofunctional alcohols,
b) branched monofunctional alcohols and
c) difunctional alcohols.

In this method the primary alcohol is preferably reacted under protective gas with continuous removal of the water that forms. The acid aluminum phyllosilicate used as a catalyst preferably has an acid load of 3 to 300 mval/100 g. Examples of aluminum phyllosilicates are talc as well as clays with a leaf structure such as kaolinite, montmorillonite, bentonites and hectorites. It is useful to continue the reaction with removal of water until no further water is released. The reaction times are usually in the range from 2 to 48 hours. The catalyst is then removed by filtration, for example. The degree of oligomerization of the poly-α-olefins is in the range from 1 to 10. The degree of oligomerization can be selectively adjusted by returning the olefins entrained by the continuous removal of water to the reaction mixture; this leads to higher degrees of oligomerization. The poly-α-olefins obtained are odorless and colorless or yellowish products, which can be liquid or solid. A precise structural formula cannot be given for the poly-α-olefins obtained, because under the dehydrating conditions of polymerization the primary alcohols in question are isomerized into a very wide variety of unsaturated monomers, which then polymerize with one another.

The cited primary alcohols can be used individually or mixed together. While the alkyl residue of the alcohols of group b) is branched, the alkyl residues of the primary alcohols of groups a) and c) can either be straight-chain or branched. The unsaturated alcohols can be mono- or polyunsaturated and are in particular olefinically unsaturated.

Preferred cosmetic compositions are those in which the primary alcohol has 6 to 72 carbon atoms and in particular 6 to 24 carbon atoms.

A linear alcohol is preferably used as the alcohol of group a). Examples of unsaturated monofunctional alcohols of group a) are 10-undecen-1-ol, oleyl alcohol, elaidyl alcohol, ricinol alcohol, linoleyl alcohol, linolenyl alcohol, gadoleyl alcohol, erucic alcohol and brassidyl alcohol.

An alcohol selected from the group of branched alcohols having b1) at least one methyl group and in particular 1 to 6 methyl branchings in the alkyl residue, b2) a $C_2$-$C_{18}$ branching in the alkyl residue and b3) a $C_2$-$C_{18}$ branching in α-position to the terminal $CH_2OH$ group is preferably used as the alcohol of group b). In the case of group b1) with at least one methyl branching in the alkyl group the methyl residue can be positioned at any point in the alkyl chain. Suitable examples are isooctyl alcohol, isononyl alcohol, isostearyl alcohol or isotridecyl alcohol. Of these, isononyl alcohol is particularly preferred. Where a plurality of methyl groups is present, their number is preferably 2 to 6, distributed arbitrarily over the alkyl residue of the alcohol. In the case of alcohols of group b2) with a $C_2$-$C_{18}$ alkyl group as the branching, there are preferably no further branchings in the alkyl residue of the alcohol.

Further suitable primary monofunctional branched alcohols are the Guerbet alcohols familiar to the person skilled in the art, which are known to be accessible via dimerization of fatty alcohols and are characterized structurally by having a relatively long alkyl residue, preferably with 2 to 18 carbon atoms, in α-position to the terminal $CH_2OH$ group. Suitable Guerbet alcohols are 2-hexyldecanol, 2-butyloctanol, 2-octyldodecanol and 2-hexyldecyl palmitate/stearate, 2-ethylhexanol and 2-propylheptanol. 2-Ethylhexyl alcohol is preferred.

Saturated or unsaturated diols can be used as alcohols of group c), in other words difunctional alcohols (having 2 hydroxyl groups), such as 1,5-pentanediol, 1,8-octanediol, 1,6-hexanediol, 1,10-decanediol, 1,12-dodecanediol, 1,12-octadecanediol or the dimer diols known to the person skilled in the art.

The poly-α-olefins can be used in the particles according to the invention in unsaturated form. However, because of the better resistance to oxidation, it is preferable to hydrogenate the poly-α-olefins following the dehydrating polymerization and to use them in hydrogenated (cured) form in the particles according to the invention.

This can be carried out in a manner known per se at temperatures in the range from 150° C. to 250° C., preferably 190° C. to 210° C., and under pressures from 20 to 150 bar (low-pressure method) or from 150 to 350 bar (high-pressure method). The hydrogenating catalysts known from the prior art, such as nickel or noble metal catalysts, in particular based on platinum or palladium, are suitable as catalysts. Palladium catalysts have proved to be particularly suitable noble metal catalysts, in particular palladium on carbon. The catalyst can be added to the poly-α-olefins in the form of a suspension or in solid form and in conventional amounts which for the preferred palladium on carbon are in the range from 0.001 to 5 wt. %, calculated as palladium. It is also possible, however, to provide the catalyst on a solid support such as activated carbon, graphite, kieselguhr, silica gel, spinel, aluminum oxide or ceramic materials. Nickel catalysts, for example suspended nickel such as Nysofact 101 I a (Engelhard), have likewise proved suitable, preferably used in amounts from 0.01 to 5 wt. %, relative to nickel.

As already mentioned, the poly-α-olefins described are colorless to slightly yellowish, virtually odorless compounds having high spreading values, typically greater than 1000 $mm^2/10$ minutes, and preferably greater than 1600 $mm^2/10$ minutes (definition according to Zeidler). Where mention is made in general terms below to poly-α-olefins, both hydrogenated and non-hydrogenated compounds are meant.

The property profile of the particles according to the invention can be varied by the choice of polyalphaolefins. Particles according to the invention are preferred in which the at least one polyalphaolefin wax is selected from polyalphaolefin waxes having a melting point in the range from 30 to 75° C., preferably 35 to 60° C., particularly preferably 40 to 55° C., exceptionally preferably 40 to 48° C., measured in accordance with ASTM D 36.

The particles according to the invention contain, relative to their weight, 10 to 70 wt. % of one or more cosmetic active agents, selected from fragrances, cooling active agents and mixtures of fragrances and cooling active agents.

Examples of scent and fragrance compounds of the ester type are benzyl acetate, phenoxyethyl isobutyrate, p-tert-butyl cyclohexyl acetate, linalyl acetate, dimethyl benzyl carbinyl acetate (DMBCA), phenylethyl acetate, benzyl acetate, ethyl methyl phenyl glycinate, allyl cyclohexyl propionate, styrallyl propionate, benzyl salicylate, cyclohexyl salicylate, floramat, melusat and jasmecyclate. Examples of scent and fragrance compounds of the ether type are benzyl ethyl ethers and ambroxan, examples of scent and fragrance compounds of the aldehyde type are the linear alkanals having 8-18 C atoms, citral, citronellal, citronellyl oxyacetaldehyde, cyclamen aldehyde, lilial and bourgeonal, examples of scent and fragrance compounds of the ketone type are ionones, alpha-isomethyl ionone and methyl cedryl ketone, examples of scent and fragrance compounds of the alcohol type are anethol, citronellol, eugenol, geraniol, linalool, phenylethyl alcohol and terpineol, examples of scent and fragrance compounds of the terpene type are limonene and pinene. Examples of scent and fragrance compounds are pine oil, citrus oil, jasmine oil, patchouli oil, rose oil, ylang-ylang oil, muscatel sage oil, chamomile oil, clove oil, mint oil, cinnamon leaf oil, lime blossom oil, juniper berry oil, vetiver oil, olibanum oil, galbanum oil, laudanum oil, orange blossom oil, neroli oil, orange peel oil and sandalwood oil, also the essential oils such as angelica root oil, aniseed oil, arnica flower oil, basil oil, bay oil, bergamot oil, champaca flower oil, noble fir oil, noble fir cone oil, elemi oil, eucalyptus oil, fennel oil, spruce needle oil, geranium oil, gingergrass oil, guaiac wood oil, gurjun balsam oil, helichrysum oil, hon-sho oil, ginger oil, iris oil, cajeput oil, calamus oil, chamomile oil, camphor oil, cananga oil, cardamom oil, cassia oil, pine needle oil, copaiba balsam oil, coriander oil, spearmint oil, caraway oil, cumin oil, lavender oil, lemongrass oil, lime oil, mandarin oil, melissa oil, musk seed oil, myrrh oil, clove oil, niaouli oil, orange oil, origanum oil, palmarosa oil, patchouli oil, Peru balsam oil, petitgrain oil, pepper oil, peppermint oil, pimento oil, pine oil, rose oil, rosemary oil, sandalwood oil, celery oil, spike lavender oil, star anise oil, turpentine oil, thuja oil, thyme oil, verbena oil, juniper berry oil, wormwood oil, wintergreen oil, hyssop oil, cinnamon oil, citronella oil, lemon oil and cypress oil. Further scent and fragrance compounds are ambrettolide, α-amylcinnamaldehyde, anethol, anisaldehyde, anisic alcohol, anisol, methyl anthranilate, acetophenone, benzyl acetone, benzaldehyde, ethyl benzoate, benzophenone, benzyl alcohol, benzyl acetate, benzyl benzoate, benzyl formate, benzyl valerianate, borneol, bornyl acetate, α-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptine carboxylate, heptaldehyde, hydroquinone dimethyl ether, hydroxycinnamaldehyde, hydroxycinnamic alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methyl methyl anthranilate, p-methyl acetophenone, methyl chavicol, p-methyl quinoline, methyl-β-naphthyl ketone, methyl-n-nonyl acetaldehyde, methyl-n-nonyl ketone, muscone, β-naphthol ethyl ether, β-naphthol methyl ether, nerol, nitrobenzene, n-nonyl aldehyde, nonyl alcohol, n-octyl aldehyde, p-oxyacetophenone, pentadecanolide, β-phenylethyl alcohol, phenyl acetaldehyde dimethyl acetal, phenyl acetic acid, pulegone, safrole, isoamyl salicylate, methyl salicylate, hexyl salicylate, cyclohexyl salicylate, santalol, skatole, terpineol, thymene, thymol, gamma-undecalactone, vanillin, veratrum aldehyde, cinnamaldehyde, cinnamyl alcohol, cinnamic acid, ethyl cinnamate and benzyl cinnamate.

Further (more highly volatile) fragrances are alkyl isothiocyanates (alkyl mustard oils), butanedione, limonene, linalool, linalyl acetate and propionate, methyl-n-heptenone, phellandrene, phenylacetaldehyde, terpinyl acetate, citral and citronellal.

Mixtures of different scents which together generate an attractive scent note are preferably used.

Suitable perfume oils can also contain natural fragrance mixtures, such as are obtainable from plant or animal sources, for example pine, citrus, jasmine, rose, lily or ylang-ylang oil. Low-volatility essential oils, which are mostly used as aroma components, are also suitable as perfume oils, for example sage oil, chamomile oil, melissa oil, mint oil, cinnamon leaf oil, lime blossom oil, juniper berry oil, vetiver oil, olibanum oil, galbanum oil, laudanum oil, clove oil, iso-eugenol, thyme oil, bergamot oil, geranium oil and rose oil.

According to the invention compounds which, like l-menthol, stimulate the heat receptors in the skin and mucous membranes such that a cool sensory impression is formed, are to be considered as the cooling active agent. In particular, the CMR-1 receptor (cold- and menthol-sensitive receptor), which belongs to the family of TRP channels, is stimulated by the cooling active agents, producing an impression of coldness.

Suitable cooling active agents according to the invention are selected from 2-isopropyl-N,2,3-trimethylbutyramide (FEMA 3804), N-ethyl-p-menthane-3-carboxamide (FEMA 3455), in particular 1R,3R,4S—N-ethyl-p-menthane-3-carboxamide, ethyl-3-(p-menthane-3-carboxamido)acetate (FEMA 4309), (1R,2S,5R)—N-(4-methoxyphenyl)-p-menthane carboxamide (FEMA 4681), N-ethyl-2,2-diisopropylbutanamide (FEMA 4557), N-cyclopropyl-5-methyl-2-isopropylcyclohexane carbon carboxamide (FEMA 4693), N-(4-cyanomethylphenyl)-p-menthane carboxamide (FEMA 4496), N-(2-(pyridin-2-yl)ethyl)-3-p-menthane carboxamide (FEMA 4549), N-(2-hydroxyethyl)-2-isopropyl-2,3-dimethylbutanamide (FEMA 4602), N-(1,1-dimethyl-2-hydroxyethyl)-2,2-diethylbutanamide (FEMA 4603), (2S, 5R)—N-[4-(2-amino-2-oxoethyl)phenyl]-p-menthane carboxamide (FEMA 4684), 2-[(2-p-menthoxy)ethoxy]ethanol (FEMA 4718), (2,6-diethyl-5-isopropyl-2-methyltetrahydropyran (FEMA 4680), 3-(1-menthoxy)-2-methylpropane-1,2-diol (FEMA 3849), p-menthane-3,8-diol, in particular (+)-cis-p-menthane-3,8-diol and (−)-trans-p-menthane-3,8-diol as well as mixtures of (+)-cis-p-menthane-3, 8-diol and (−)-trans-p-menthane-3,8-diol, in particular a mixture in the weight ratio 62:38 (FEMA 4053), (1R,3R, 4S)-3-menthyl-3,6-dioxaheptanoate, (1R,2S,5R)-3-menthyl methoxyacetate, (1R,2S,5R)-3-menthyl-3,6,9-trioxadecanoate, (1R,2S,5R)-3-menthyl-3,6,9-trioxadecanoate, (1R,2S, 5R)-3-menthyl-(2-hydroxyethoxy)acetate, (1R,2 S,5R)-menthyl-11-hydroxy-3,6,9-trioxaundecanoate, (−)-cubebol (FEMA 4497), N-(4-cyanomethylphenyl)-p-menthane carboxamide, N,N-dimethyl menthyl succinamide (2-isopropyl-5-methylcyclohexyl-4-(dimethylamino)-4-oxobutanoate, FEMA 4230), 6-isopropyl-3,9-dimethyl-1,4-dioxaspiro [4.5]decan-2-one (FEMA 4285), N-benzo[1,3]-dioxol-5-yl-3-p-menthane carboxamide, N-benzoxazol-4-yl-3-p-menthane carboxamide, N-4-([1,2,4]-triazol-1-yl)-phenyl-3-p-menthane carboxamide, N-4-(pyrazol-1-yl)-phenyl-3-p-menthane carboxamide, N-(1-isopropyl-1,2-dimethylpropyl)-1,3-benzodioxole-5-carboxamide, mixtures of 2,2,5,6,6-pentamethyl-2,3,6,6a-tetrahydropentalen-3a(1H)-ol and 5-(2-hydroxy-2-methylpropyl)-3,4,4-trimethylcyclopent-2-en-1-one in accordance with US 20070274928 A1, (1S,2S,5R)—N-(4-(cyanomethyl)phenyl)-2-isopropyl-5-methylcyclohexane carboxamide, neo-menthyl lactate (2S), neo-menthyl lactate acetate [(1S,2S, 5R)-2-isopropyl-5-methylcyclohexyl-2(S)-acetoxypropanoate] and 1-isopropyl-4-methylbicyclo[2.2.2] oct-5-ene-2,3-dicarbinol in accordance with WO 2007/022651 and mixtures thereof. If the aforementioned compounds are not designated more specifically in terms of their stereoisomers, the all-equatorial isomers of the aforementioned compounds should be regarded as being preferred.

Menthol, isopulegol and menthol derivatives, for example menthyl lactate, menthyl pyrrolidone carboxylic acid, menthyl methyl ether, menthoxypropanediol, menthone glycerol acetal (9-methyl-6-(1-methylethyl)-1,4-dioxaspiro(4.5)decane-2-methanol), monomenthyl succinate and 2-hydroxymethyl-3,5,5-trimethyl cyclohexanol, are preferred as cooling active agents. Menthol, isopulegol, methyl lactate, menthoxypropanediol and menthyl pyrrolidone carboxylic acid are particularly preferred.

Preferred compositions according to the invention contain one or more cooling active agents in a total amount from 0.01 to 5 wt. %, preferably in a total amount from 0.05 to 2 wt. %, particularly preferably in a total amount from 0.1 to 1 wt. %, exceptionally preferably in a total amount from 0.2 to 0.6 wt. %, the stated amounts relating to the weight of the composition.

Preferred particles according to the invention contain 15 to 65 wt. %, more preferred particles 20 to 60 wt. %, still more preferred particles 22.5 to 55 wt. % and particles that are preferred in particular 25 to 50 wt. % of one or more cosmetic active agents selected from fragrances, cooling active agents and mixtures of fragrances and cooling active agents.

In summary, preferred particles according to the invention are characterized in that the total proportion of polyalphaolefin wax(es) is 50 to 75 wt. % and the total proportion of at least one cosmetic active agent selected from fragrances, cooling active agents and mixtures of fragrances and cooling active agents is 25 to 50 wt. %, relative in each case to the particle weight.

The particles according to the invention (i.e. polymer plus active agent) preferably also have certain physical properties which can in turn be controlled by means of the type of polymer and active agent and by their relative proportion to one another. Preferred particles according to the invention are characterized by a melting point in the range from 25 to 40° C., preferably 26 to 35° C., particularly preferably 27 to 33° C., exceptionally preferably 29 to 31° C., measured in accordance with ASTM D 36.

In order to achieve optimal results in terms of the subsequent application form in cosmetics, it has proved particularly suitable for the particles according to the invention to have a number-average particle diameter in the range from 50 nm to 100 μm, preferably 100 nm to 80 μm, particularly preferably 500 nm to 50 μm, exceptionally preferably 1 μm to 30 μm. The particles according to the invention are suitable in particular for use in cosmetic compositions. They have proved particularly effective in deodorant and antiperspirant compositions. In this specific area of application the roll-on presentation form has proved a particularly suitable area of use for the particles according to the invention.

The present invention also provides a cosmetic composition containing water and 0.01 to 10 wt. %, relative to the weight of the cosmetic composition, of one or more particles according to the invention.

The compositions according to the invention preferably contain 40 to 90 wt. %, particularly preferably 50 to 85 wt. %, exceptionally preferably 60 to 80 wt. %, more exceptionally preferably 65 to 75 wt. % of water, relative in each case to the total weight of the composition. Within the meaning of the present application, "water" is understood to mean "free water", i.e. water which is not contained in the antiperspirant composition in the form of water of crystallization, water of hydration or similarly molecularly bound water. The content of water of crystallization, water of hydration or similarly molecularly bound water that may be contained in the constituents used, in particular in the sweat-inhibiting active agents, does not constitute free water within the meaning of the present application. Free water is water which is contained in the composition according to the invention as a solvent or as a solvent constituent of other active agents, for example.

As has already been mentioned, preferred compositions according to the invention are deodorants and/or antiperspirants. Preferred cosmetic compositions according to the invention are characterized in that at least one antiperspirant active agent is contained.

Preferred antiperspirant active agents according to the invention are selected from the water-soluble astringent inorganic and organic salts of aluminum, zirconium and zinc and any mixtures of these salts. According to the invention water solubility is understood to mean a solubility of at least 5 wt. % at 20° C., in other words amounts of at least 5 g of the antiperspirant active agent are soluble in 95 g of water at 20° C. Particularly preferred antiperspirant active agents are selected from aluminum chlorohydrate, in particular aluminum chlorohydrate of the general formula $[Al_2(OH)_5Cl.1\text{-}6H_2O]_n$, preferably $[Al_2(OH)_5Cl.2\text{-}3H_2O]_n$, which can be present in non-activated or in activated (depolymerized) form, and aluminum chlorohydrate of the general formula $[Al_2(OH)_4Cl_2.1\text{-}6H_2O]_n$, preferably $[Al_2(OH)_4Cl_2.2\text{-}3H_2O]_n$, which can be present in non-activated or in activated (depolymerized) form.

Also preferred are aluminum sesquichlorohydrate, aluminum dichlorohydrate, aluminum chlorohydrex propylene glycol (PG) or aluminum chlorohydrex polyethylene glycol (PEG), aluminum or aluminum zirconium glycol complexes, e.g. aluminum or aluminum zirconium propylene glycol complexes, aluminum sesquichlorohydrex PG or aluminum sesquichlorohydrex PEG, aluminum PG dichlorohydrex or aluminum PEG dichlorohydrex, aluminum hydroxide, selected furthermore from aluminum zirconium chlorohydrates, such as aluminum zirconium trichlorohydrate, aluminum zirconium tetrachlorohydrate, aluminum zirconium pentachlorohydrate, aluminum zirconium octachlorohydrate, aluminum zirconium chlorohydrate glycine complexes such as aluminum zirconium trichlorohydrex glycine, aluminum zirconium tetrachlorohydrex glycine, aluminum zirconium pentachlorohydrex glycine, aluminum zirconium octachlorohydrex glycine, potassium aluminum sulfate ($KAl(SO_4)_2.12H_2O$, alum), aluminum undecylenoyl collagen amino acid, sodium aluminum lactate+aluminum sulfate, sodium aluminum chlorohydroxylactate, aluminum bromohydrate, aluminum chloride, complexes of zinc and sodium salts, complexes of lanthanum and cerium, aluminum salts of lipoamino acids, aluminum sulfate, aluminum lactate, aluminum chlorohydroxyallantoinate, sodium aluminum chlorohydroxylactate, zinc chloride, zinc sulfocarbolate, zinc sulfate, zirconyl oxyhalides, in particular zirconyl oxychlorides, zirconyl hydroxyhalides, in particular zirconyl hydroxychlorides (zirconium chlorohydrate). Antiperspirant active agents that are particularly preferred according to the invention are selected from "activated" aluminum and aluminum zirconium salts, which are also referred to as antiperspirant active agents with enhanced activity. Such active agents are known in the prior art and are also available commercially. Activated aluminum and aluminum zirconium salts typically have an HPLC peak 4 to peak 3 surface area ratio of at least 0.4, preferably at least 0.7, particularly preferably at least 0.9, wherein at least 70% of the aluminum can be assigned to these peaks.

Activated aluminum and aluminum zirconium salts do not necessarily have to be used as a spray-dried powder. Sweat-inhibiting active agents that are likewise preferred according to the invention are non-aqueous solutions or solubilizates of an activated sweat-inhibiting aluminum or aluminum zirconium salt, which are stabilized against loss of activation by the rapid degradation of the HPLC peak 4 to peak 3 surface area ratio of the salt by the addition of an effective amount of a polyhydric alcohol having 3 to 6 carbon atoms and 3 to 6 hydroxyl groups, preferably propylene glycol, sorbitol and pentaerythritol. Compositions are preferred for example that contain in percent by weight (USP): 18 to 45 wt. % of an activated aluminum or aluminum zirconium salt, 55 to 82 wt. % of at least one anhydrous polyhydric alcohol having 3 to 6 carbon atoms and 3 to 6 hydroxyl groups, preferably propylene glycol, butylene glycol, diethylene glycol, dipropylene glycol, glycerol, sorbitol and pentaerythritol, particularly preferably propylene glycol.

Complexes of activated sweat-inhibiting aluminum or aluminum zirconium salts with a polyhydric alcohol containing 20 to 50 wt. %, particularly preferably 20 to 42 wt. %, of activated sweat-inhibiting aluminum or aluminum zirconium salt and 2 to 16 wt. % of molecularly bound water are also particularly preferred, wherein the remainder up to 100 wt. % is made up by at least one polyhydric alcohol having 3 to 6 carbon atoms and 3 to 6 hydroxyl groups. Propylene glycol, propylene glycol/sorbitol mixtures and propylene glycol/pentaerythritol mixtures are preferred alcohols of this type.

Further preferred sweat-inhibiting active agents are basic calcium aluminum salts. These salts are produced by reacting calcium carbonate with aluminum chlorohydroxide or aluminum chloride and aluminum powder or by adding calcium chloride dihydrate to aluminum chlorohydroxide. Further preferred sweat-inhibiting active agents are aluminum zirconium complexes buffered with salts of amino acids, in particular with alkali and alkaline-earth glycinates.

Further preferred sweat-inhibiting active agents are activated aluminum or aluminum zirconium salts containing 5 to 78 wt. % (USP) of an activated sweat-inhibiting aluminum or aluminum zirconium salt, an amino acid or hydroxyalkanoic acid in an amount to provide a weight ratio of (amino acid or hydroxyalkanoic acid) to (Al+Zr) of 2:1 to 1:20 and preferably 1:1 to 1:10, and a water-soluble calcium salt in an amount to provide a weight ratio of Ca to (Al+Zr) of 1:1 to 1:28 and preferably 1:2 to 1:25. Particularly preferred solid activated sweat-inhibiting salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water (water of hydration), also sufficient water-soluble calcium salt that the weight ratio of Ca to (Al+Zr) is 1:1 to 1:28, preferably 1:2 to 1:25, and sufficient amino acid that the weight ratio of amino acid to (Al+Zr) is 2:1 to 1:20, preferably 1:1 to 1:10.

Further particularly preferred solid sweat-inhibiting activated salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water (water of hydration), also sufficient water-soluble calcium salt that the weight ratio of Ca to (Al+Zr) is 1:1 to 1:28, preferably 1:2 to 1:25, and sufficient glycine that the weight ratio of glycine to (Al+Zr) is 2:1 to 1:20, preferably 1:1 to 1:10. Further particularly preferred solid sweat-inhibiting activated salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water (water of hydration), also sufficient water-soluble calcium salt that the weight ratio of Ca to (Al+Zr) is 1:1 to 1:28, preferably 1:2 to 1:25, and sufficient hydroxyalkanoic acid that the weight ratio of hydroxyalkanoic acid to (Al+Zr) is 2:1 to 1:20, preferably 1:1 to 1:10. Preferred water-soluble calcium salts for stabilizing the sweat-inhibiting salts are selected from calcium chloride, calcium bromide, calcium nitrate, calcium citrate, calcium formate, calcium acetate, calcium gluconate, calcium ascorbate, calcium lactate, calcium glycinate, calcium carbonate, calcium sulfate, calcium hydroxide, and mixtures thereof.

Preferred amino acids for stabilizing the sweat-inhibiting salts are selected from glycine, alanine, leucine, isoleucine, β-alanine, valine, cysteine, serine, tryptophan, phenylalanine, methionine, β-amino-n-butanoic acid and γ-amino-n-butanoic acid and the salts thereof, in each case in the d form, l form or dl form; glycine is particularly preferred. Preferred hydroxyalkanoic acids for stabilizing the sweat-inhibiting salts are selected from glycolic acid and lactic acid.

Further preferred sweat-inhibiting active agents are activated aluminum or aluminum zirconium salts containing 5 to 78 wt. % (USP) of an activated sweat-inhibiting aluminum or aluminum zirconium salt, an amino acid or hydroxyalkanoic acid in an amount to provide a weight ratio of (amino acid or hydroxyalkanoic acid) to (Al+Zr) of 2:1 to 1:20 and preferably 1:1 to 1:10, and a water-soluble strontium salt in an amount to provide a weight ratio of Sr to (Al+Zr) of 1:1 to 1:28 and preferably 1:2 to 1:25. Particularly preferred solid sweat-inhibiting activated salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient amino acid that the weight ratio of amino acid to (Al+Zr) is 2:1 to 1:20, preferably 1:1 to 1:10.

Further particularly preferred solid sweat-inhibiting activated salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient glycine that the weight ratio of glycine to (Al+Zr) is 2:1 to 1:20, preferably 1:1 to 1:10.

Further particularly preferred solid sweat-inhibiting activated salt compositions contain 48 to 78 wt. % (USP), preferably 66 to 75 wt. % of an activated aluminum or aluminum zirconium salt and 1 to 16 wt. %, preferably 4 to 13 wt. % of molecularly bound water, also sufficient water-soluble strontium salt that the weight ratio of Sr to (Al+Zr) is 1:1 to 1:28, preferably 1:2 to 1:25, and sufficient hydroxyalkanoic acid that the weight ratio of hydroxyalkanoic acid to (Al+Zr) is 2:1 to 1:20, preferably 1:1 to 1:10.

Further preferred activated aluminum salts are those of the general formula $Al_2(OH)_{6-a}X_a$, in which X is Cl, Br, 1 or $NO_3$ and "a" is a value from 0.3 to 5, preferably from 0.8 to 2.5 and particularly preferably 1 to 2, such that the molar ratio of Al to X is 0.9:1 to 2.1:1. These salts generally contain a little associatively bound water of hydration, typically 1 to 6 mol of water per mol of salt. Aluminum chlorohydrate is particularly preferred (i.e. X is Cl in the above formula), and specifically 5/6-basic aluminum chlorohydrate, wherein "a" is 1, such that the molar ratio of aluminum to chlorine is 1.9:1 to 2.1:1.

Preferred activated aluminum zirconium salts are those that are mixtures or complexes of the aluminum salts described above with zirconium salts of the formula $ZrO(OH)_{2-pb}Y_b$, in which Y is Cl, Br, 1, $NO_3$ or $SO_4$, b is a rational number from 0.8 to 2 and p is the valence of Y. The zirconium salts generally likewise contain a little associatively bound water of hydration, typically 1 to 7 mol of water per mol of salt. The zirconium salt is preferably zirconyl hydroxychloride of the formula $ZrO(OH)_{2-b}Cl_b$, in which b is a rational number from 0.8 to 2, preferably 1.0 to 1.9. Preferred aluminum zirconium salts have a molar Al:Zr ratio of 2 to 10 and a metal to (X+Y) ratio of 0.73 to 2.1, preferably 0.9 to 1.5. A particularly preferred salt is aluminum zirconium chlorohydrate (i.e. X and Y are Cl) with an Al:Zr ratio of 2 to 10 and a molar metal to Cl ratio of 0.9 to 2.1. The term aluminum zirconium chlorohydrate comprises the tri-, tetra-, penta- and octachlorohydrate forms.

Preferred zirconium salts according to the invention have the general formula $ZrO(OH)_{2-a}Cl_a \cdot xH_2O$ where a=1.5 to 1.87; x=1 to 7, with a and x being rational numbers.

The sweat-inhibiting active agents can be present both in solubilized and in undissolved, suspended form. If the sweat-inhibiting active agents are present suspended in a water-immiscible carrier, it is preferable for reasons of product stability for the active agent particles to have a number-average particle size of 0.1 to 200 µm, preferably 1 to 50 µm, particularly preferably 3 to 20 µm and exceptionally preferably 5 to 10 µm.

Preferred aluminum salts and aluminum zirconium salts have a molar metal to chloride ratio of 0.9 to 1.3, preferably 0.9 to 1.1, particularly preferably 0.9 to 1.0.

Preferred aluminum zirconium chlorohydrates generally have the empirical formula $Al_nZr(OH)_{[3n+4-m(n+1)]}(Cl)_{[m(n+1)]}$ where n=2.0 to 10.0, preferably 3.0 to 8.0, m=0.77 to 1.11 (corresponding to a molar metal (Al+Zr) to chloride ratio of 1.3 to 0.9), preferably m=0.91 to 1.11 (corresponding to M:Cl=1.1 to 0.9), and particularly preferably m=1.00 to 1.11 (corresponding to M:Cl=1.0 to 0.9), furthermore very preferably m=1.02 to 1.11 (corresponding to M:Cl=0.98 to 0.9) and very preferably m=1.04 to 1.11 (corresponding to M:Cl=0.96 to 0.9).

These salts generally contain a little associatively bound water of hydration, typically 1 to 6 mol of water per mol of salt, corresponding to 1 to 16 wt. %, preferably 4 to 13 wt. % of water of hydration.

The preferred aluminum zirconium chlorohydrates are conventionally associated with an amino acid to prevent polymerization of the zirconium species during production. Preferred stabilizing amino acids are selected from glycine, alanine, leucine, isoleucine, β-alanine, cysteine, valine, serine, tryptophan, phenylalanine, methionine, β-amino-n-butanoic acid and γ-amino-n-butanoic acid and the salts thereof, in each case in the d form, l form or dl form; glycine is particularly preferred. The amino acid is contained in the salt in an amount from 1 to 3 mol, preferably 1.3 to 1.8 mol, per mol of zirconium. Preferred sweat-inhibiting salts are aluminum zirconium tetrachlorohydrate (Al:Zr=2-6; M:Cl=0.9-1.3), in particular salts with a molar metal to chloride ratio of 0.9 to 1.1, preferably 0.9 to 1.0.

Also preferred according to the invention are aluminum zirconium chlorohydrate glycine salts stabilized with betaine (($CH_3)_3N^+$—$CH_2$—$COO^-$). Particularly preferred corresponding compounds have a molar total (betaine+glycine)/Zr ratio of (0.1 to 3.0):1, preferably (0.7 to 1.5):1, and a molar ratio of betaine to glycine of at least 0.001:1. In a particularly preferred embodiment according to the invention an "activated" salt is contained as a particularly effective antiperspirant salt, in particular one with a high HPLC peak 5 aluminum content, in particular with a peak 5 surface area of at least 33%, particularly preferably at least 45%, relative to the total surface area under peaks 2 to 5, measured by HPLC of a 10 wt. % aqueous solution of the active agent under conditions in which the aluminum species is dissolved into at least 4 successive peaks (referred to as peaks 2 to 5). Preferred aluminum zirconium salts are those having a high HPLC peak 5 aluminum content (also known as "$E^5AZCH$"). Such activated "$E^5AZCH$" salts are also preferred in which the HPLC peak 4 to peak 3 surface area ratio is at least 0.4, preferably at least 0.7, particularly preferably at least 0.9. Further particularly preferred antiperspirant active agents are aluminum zirconium salts having a high HPLC peak 5 aluminum content which are additionally stabilized with a water-soluble strontium salt and/or with a water-soluble calcium salt.

Further preferred antiperspirant active agents are selected from astringent titanium salts. The antiperspirant active agents can be used as non-aqueous solutions or as glycolic solubilizates.

Particularly preferred compositions according to the invention are characterized in that the at least one antiperspirant active agent is contained in an amount from 3 to 27 wt. %, preferably 5 to 22 wt. % and particularly preferably 10 to 20 wt. %, relative to the total weight of active substance (USP) free from water of crystallization in the total composition.

Likewise preferred cosmetic compositions according to the invention are characterized in that at least one deodorant active agent is contained.

Preferred deodorant active agents according to the invention are odor absorbers, deodorizing ion exchangers, bacteriostatic agents, prebiotic components and enzyme inhibitors or, particularly preferably, combinations of the cited active agents. Silicates serve as odor absorbers, which at the same time advantageously also support the rheological properties of the composition according to the invention. The particularly preferred silicates according to the invention include above all phyllosilicates and of those in particular montmorillonite, kaolinite, illite, beidellite, nontronite, saponite, hectorite, bentonite, smectite and talc. Further preferred odor absorbers are for example zeolites, zinc ricinoleate, cyclodextrins, certain metal oxides, such as for example aluminum oxide, and chlorophyll. They are preferably used in an amount from 0.1 to 10 wt. %, particularly preferably 0.5 to 7 wt. % and exceptionally preferably 1 to 5 wt. %, relative in each case to the total composition.

Bacteriostatic or antimicrobial active agents are understood according to the invention to be active agents that reduce the number of skin bacteria involved in odor formation or inhibit their growth. These bacteria include inter alia various species from the group of Staphylococci, the group of Corynebacteria, Anaerococci and Micrococci.

Organohalogen compounds and organohalides, quaternary ammonium compounds, a series of plant extracts and zinc compounds are preferred in particular according to the invention as bacteriostatic or antimicrobial active agents. These include inter alia triclosan, chlorhexidine and chlorhexidine gluconate, 3,4,4'-trichlorocarbanilide, bromochlorophene, dichlorophene, chlorothymol, chloroxylenol, hexachlorophene, dichloro-m-xylenol, dequalinium chloride, domiphen bromide, ammonium phenol sulfonate, benzalkonium halides, benzalkonium cetyl phosphate, benzalkonium saccharinates, benzethonium chloride, cetyl pyridinium chloride, lauryl pyridinium chloride, lauryl isoquinolinium bromide, methyl benzethonium chloride. Phenol, phenoxyethanol, disodium dihydroxyethyl sulfosuccinyl undecylenate, sodium bicarbonate, zinc lactate, sodium phenol sulfonate and zinc phenol sulfonate, ketoglutaric acid, terpene alcohols such as for example farnesol, chlorophyllin copper complexes, α-monoalkyl glycerol ethers having a branched or linear saturated or unsaturated, optionally hydroxylated $C_6$-$C_{22}$ alkyl residue, particularly preferably α-(2-ethylhexyl)glycerol ether, available commercially as Sensiva® SC 50 (from Scülke & Mayr), carboxylic acid esters of mono-, di- and triglycerol (for example glycerol monolaurate, diglycerol monocaprinate), lantibiotics and plant extracts (for example green tea and constituents of linden blossom oil) can also be used.

Further preferred deodorant active agents are selected from components having a prebiotic effect, which are understood according to the invention to be components which inhibit only or at least predominantly the odor-forming bacteria of the skin microflora but not the desirable, i.e. non-odor-forming bacteria that belong to a healthy skin microflora. These explicitly include for example conifer extracts, in particular from the group of Pinaceae, and plant extracts from the group of Sapindaceae, Araliaceae, Lamiaceae and Saxifragaceae, in particular extracts of *Picea* spp., *Paullinia* sp., *Panax* sp., *Lamium album* or *Ribes nigrum*, and mixtures of these substances.

Further preferred deodorant active agents are selected from the bacteriostatic perfume oils and Deosafe® perfume oils available from Symrise, formerly Haarmann & Reimer.

Enzyme inhibitors include substances which inhibit the enzymes responsible for breaking down sweat, in particular arylsulfatase, β-glucuronidase, aminoacylase, esterases, lipases and/or lipoxigenase, for example trialkyl citric acid esters, in particular triethyl citrate, or zinc glycinate.

Preferred deodorant or antiperspirant compositions according to the invention are characterized in that the at least one deodorant active agent is selected from arylsulfatase inhibitors, β-glucuronidase inhibitors, aminoacylase inhibitors, esterase inhibitors, lipase inhibitors and lipoxigenase inhibitors, α-monoalkyl glycerol ethers having a branched or linear saturated or unsaturated, optionally hydroxylated $C_6$-$C_{22}$ alkyl residue, in particular α-(2-ethylhexyl)glycerol ether, phenoxyethanol, bacteriostatic perfume oils, Deosafe® perfume oils (Deosafe® is a registered trademark of Symrise, formerly Haarmann & Reimer), prebiotic components, trialkyl citric acid esters, in particular triethyl citrate, active agents that reduce the number of skin bacteria from the group of Staphylococci, Corynebacteria, Anaerococci and Micrococci involved in odor formation or inhibit their growth, zinc compounds, in particular zinc phenol sulfonate and zinc ricinoleate, organohalogen compounds, in particular triclosan, chlorhexidine, chlorhexidine gluconate and benzalkonium halides, quaternary ammonium compounds, in particular cetyl pyridinium chloride, odor absorbers, in particular silicates and zeolites, sodium bicarbonate, lantibiotics, and mixtures of the aforementioned substances.

Further preferred deodorant or antiperspirant compositions according to the invention are characterized in that the at least one deodorant active agent is contained in a total amount from 0.1 to 10 wt. %, preferably 0.2 to 7 wt. %, particularly preferably 0.3 to 5 wt. % and exceptionally preferably 0.4 to 1.0 wt. %, relative in each case to the total weight of active substance of the deodorant active agent or deodorant active agents in the total composition.

In a further particularly preferred embodiment the compositions according to the invention can contain both at least one deodorant active agent and at least one antiperspirant active agent.

The compositions according to the invention can furthermore contain at least one polymer selected from polysaccharides, esters and/or ethers thereof and mixtures thereof. Polysaccharides (also known as poly-sugars, glycanes or polyoses) are carbohydrates consisting of a large number (at least 10) monosaccharides (simple sugars) bound via a glycosidic bond. These are biopolymers containing an unknown number of monosaccharide units or a random molecular size distribution. Polysaccharides are for example glycogen, starch (amylose and amylopectin), pectins, chitin, callose and cellulose. Xanthan, for example, is an important heteropolysaccharide. Preferred compositions according to the invention are characterized in that they contain at least one polymer selected from polysaccharides, esters and/or ethers thereof and mixtures thereof, in a total amount from 0.05 to 1 wt. %, preferably 0.1 to 0.7 wt. %, particularly preferably 0.1 to 0.3 wt. %, relative in each case to the total weight of the composition.

Of the polysaccharides, esters and/or ethers thereof and mixtures thereof, cellulose and the corresponding derivatives are particularly preferred.

Preferred cellulose ethers are selected from hydroxyalkyl celluloses, in particular from hydroxyethyl cellulose, hydroxypropyl cellulose, hydroxypropyl methyl cellulose, carboxymethyl cellulose, cetyl hydroxyethyl cellulose, hydroxybutyl methyl cellulose and methyl hydroxyethyl cellulose as well as mixtures thereof. Hydroxyethyl cellulose is exceptionally preferred.

Preferred compositions according to the invention contain at least one non-ionic thickening polymer selected from cellulose and cellulose ethers and mixtures thereof, in a total amount from 0.05 to 1 wt. %, preferably 0.1 to 0.7 wt. %, particularly preferably 0.1 to 0.3 wt. %, relative in each case to the total weight of the composition.

Further preferred compositions according to the invention contain 0.05 to 1 wt. %, preferably 0.1 to 0.7 wt. %, particularly preferably 0.1 to 0.3 wt. % of hydroxyethyl cellulose, relative in each case to the total weight of the composition.

Further preferred compositions according to the invention contain, relative in each case to the total weight of the composition, 0.05 to 1.0 wt. %, preferably 0.1 to 0.8 wt. %, particularly preferably 0.2 to 0.5 wt. % of dehydroxanthan gum and 0.05 to 1 wt. %, preferably 0.1 to 0.7 wt. %, particularly preferably 0.1 to 0.3 wt. % of hydroxyethyl cellulose.

It has been found that the compositions according to the invention can additionally contain to particular advantage dehydroxanthan gum. With the combination of dehydroxanthan gum and at least one non-ionic thickening polymer selected from cellulose and cellulose ethers and mixtures thereof, the viscosities of the compositions according to the invention are in the required range from an application perspective of between 1500 and 2500 mPas, the viscosity being measured at 23° C. with a Brookfield RVF rotary viscometer, spindle 4, shear rate (rotational frequency) 20 rpm, without helipath.

The compositions according to the invention preferably contain dehydroxanthan gum in an amount from 0.05 to 1 wt. %, particularly preferably 0.1 to 0.8 wt. %, exceptionally preferably 0.2 to 0.5 wt. %, relative in each case to the total weight of the composition.

Further preferred compositions according to the invention are characterized in that dehydroxanthan gum and the total amount of non-ionic thickening polymer, selected from cellulose and cellulose ethers and mixtures thereof, are contained in a weight ratio from 1 to 2.5, preferably 1.2 to 2.0, particularly preferably 1.4 to 1.6.

Further preferred compositions according to the invention are characterized in that dehydroxanthan gum and hydroxyethyl cellulose are contained in a weight ratio from 1 to 2.5, preferably 1.2 to 2.0, particularly preferably 1.4 to 1.6.

Particularly preferred compositions according to the invention are characterized in that they contain, relative in each case to the total weight of the composition, 0.1 to 0.8 wt. % of dehydroxanthan gum and 0.1 to 0.7 wt. % of hydroxyethyl cellulose.

Preferred compositions according to the invention contain at least one oil-in-water emulsifier having an HLB value of greater than 7 to 20, which is particularly preferably selected from non-ionic oil-in-water emulsifiers having an HLB value of greater than 7 to 20.

These are emulsifiers which are generally known to the person skilled in the art, as listed for example in Kirk-Othmer, "Encyclopedia of Chemical Technology", $3^{rd}$ Edition, 1979, Volume 8, pages 913-916. For ethoxylated products the HLB value is calculated using the formula HLB= (100−L): 5, where L is the proportion by weight of lipophilic groups, i.e. fatty alkyl or fatty acyl groups, in the ethylene oxide adducts, expressed as a percentage by weight.

Further preferred antiperspirant compositions according to the invention are characterized in that at least one non-ionic emulsifier having an HLB value in the range from 12 to 18 is contained. Preferred antiperspirant compositions according to the invention are characterized in that the non-ionic oil-in-water emulsifiers having an HLB value of greater than 7 to 20 are selected from ethoxylated $C_8$-$C_{24}$ alkanols having on average 10-100 mol of ethylene oxide per mol, ethoxylated $C_8$-$C_{24}$ carboxylic acids having on average 10-100 mol of ethylene oxide per mol, sorbitan monoesters of linear saturated and unsaturated $C_{12}$-$C_{30}$ carboxylic acids ethoxylated with on average 20-100 mol of ethylene oxide per mol, which can be hydroxylated, in particular those of myristic acid, palmitic acid, stearic acid or of mixtures of these fatty acids, silicone copolyols having ethylene oxide units or ethylene oxide and propylene oxide units, alkyl mono- and oligoglycosides having 8 to 22 carbon atoms in the alkyl residue and ethoxylated analogs thereof, ethoxylated sterols, partial esters of polyglycerols having n=2 to 10 glycerol units and esterified with 1 to 4 saturated or unsaturated, linear or branched, optionally hydroxylated $C_8$-$C_{30}$ fatty acid residues, provided they have an HLB value of greater than 7 to 20, and mixtures of the aforementioned substances.

The ethoxylated $C_8$-$C_{24}$ alkanols have the formula $R^1O(CH_2CH_2O)_nH$, in which $R^1$ denotes a linear or branched alkyl and/or alkenyl residue having 8-24 carbon atoms and n, the average number of ethylene oxide units per molecule, denotes numbers from 10 to 100, preferably 10 to 30 mol of ethylene oxide, with 1 mol of caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof. Adducts of 10-100 mol of ethylene oxide with technical fatty alcohols having 12-18 carbon atoms, such as for example coconut, palm, palm kernel or tallow fatty alcohol, are also suitable.

The ethoxylated $C_8$-$C_{24}$ carboxylic acids have the formula $R^1O(CH_2CH_2O)_nH$, in which $R^1O$ denotes a linear or branched, saturated or unsaturated acyl residue having 8-24 carbon atoms and n, the average number of ethylene oxide units per molecule, denotes numbers from 10 to 100, preferably 10 to 30 mol of ethylene oxide, with 1 mol of caprylic acid, 2-ethylhexanoic acid, capric acid, lauric acid, isotridecanoic acid, myristic acid, cetylic acid, palmitoleic acid, stearic acid, isostearic acid, oleic acid, elaidic acid, petroselic acid, arachidic acid, gadoleic acid, behenic acid, erucic acid and brassidic acid and technical mixtures thereof. Adducts of 10-100 mol of ethylene oxide with technical fatty acids having 12-18 carbon atoms, such as coconut, palm, palm kernel or tallow fatty acid, are also suitable. PEG-50 monostearate, PEG-100 monostearate, PEG-50 monooleate, PEG-100 monooleate, PEG-50 monolaurate and PEG-100 monolaurate are particularly preferred.

The $C_{12}$-$C_{18}$ alkanols or $C_{12}$-$C_{18}$ carboxylic acids, each having 10-30 units of ethylene oxide per molecule, and mixtures of these substances, in particular ceteth-10, ceteth-12, ceteth-20, ceteth-30, steareth-10, steareth-12, steareth-20, steareth-21, steareth-30, ceteareth-10, ceteareth-12, ceteareth-20, ceteareth-30, laureth-12 and beheneth-20, are particularly preferably used.

Preferred sorbitan monoesters of linear saturated and unsaturated $C_{12}$-$C_{30}$ carboxylic acids ethoxylated with on average 20-100 mol of ethylene oxide per mol, which can be hydroxylated, are selected from polysorbate-20, polysorbate-40, polysorbate-60 and polysorbate-80.

$C_8$-$C_{22}$ alkyl mono- and oligoglycosides are moreover preferably used. $C_8$-$C_{22}$ alkyl mono- and oligoglycosides are known, commercial surfactants and emulsifiers. They are produced in particular by reacting glucose or oligosaccharides with primary alcohols having 8-22 carbon atoms. Regarding the glycoside residue, both monoglycosides in which a cyclic sugar residue is glycosidically bound to the fatty alcohol and oligomeric glycosides having a degree of oligomerization of up to around 8, preferably 1 to 2, are suitable. The degree of oligomerization is a statistical mean based on a conventional homolog distribution for technical products. Products available under the trademark Plantacare® from BASF contain a glucosidically bound $C_8$-$C_{16}$ alkyl group at an oligoglucoside residue whose average degree of oligomerization is 1 to 2, in particular 1.2 to 1.4. Particularly preferred $C_8$-$C_{22}$ alkyl mono- and oligoglycosides are selected from octyl glucoside, decyl glucoside, lauryl glucoside, palmityl glucoside, isostearyl glucoside, stearyl glucoside, arachidyl glucoside and behenyl glucoside and mixtures thereof. The acyl glucamides derived from glucamine are also suitable as non-ionic oil-in-water emulsifiers.

Ethoxylated sterols, in particular ethoxylated soy sterols, are also suitable oil-in-water emulsifiers according to the invention. The degree of ethoxylation should be greater than 5, preferably at least 10 in order to have an HLB value greater than 7. Suitable commercial products are for example PEG-10 soy sterol, PEG-16 soy sterol and PEG-25 soy sterol.

Partial esters of polyglycerols having 2 to 10 glycerol units and esterified with 1 to 4 saturated or unsaturated linear or branched, optionally hydroxylated $C_8$-$C_{30}$ fatty acid residues are also preferably used, provided they have an HLB value of greater than 7 to 20. Diglycerol monocaprylate, diglycerol monocaprate, diglycerol monolaurate, triglycerol monocaprylate, triglycerol monocaprate, triglycerol monolaurate, tetraglycerol monocaprylate, tetraglycerol monocaprate, tetraglycerol monolaurate, pentaglycerol monocaprylate, pentaglycerol monocaprate, pentaglycerol monolaurate, hexaglycerol monocaprylate, hexaglycerol monocaprate, hexaglycerol monolaurate, hexaglycerol monomyristate, hexaglycerol monostearate, decaglycerol monocaprylate, decaglycerol monocaprate, decaglycerol monolaurate, decaglycerol monomyristate, decaglycerol monoisostearate, decaglycerol monostearate, decaglycerol monooleate, decaglycerol monohydroxystearate, decaglycerol dicaprylate, decaglycerol dicaprate, decaglycerol dilaurate, decaglycerol dimyristate, decaglycerol diisostearate, decaglycerol distearate, decaglycerol dioleate, decaglycerol dihydroxystearate, decaglycerol tricaprylate, decaglycerol tricaprate, decaglycerol trilaurate, decaglycerol trimyristate, decaglycerol triisostearate, decaglycerol tristearate, decaglycerol trioleate and decaglycerol trihydroxystearate are particularly preferred.

Particularly preferred antiperspirant compositions according to the invention contain at least one oil-in-water emulsifier having an HLB value of greater than 7 to 20 in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Further particularly preferred antiperspirant compositions according to the invention contain at least one non-ionic oil-in-water emulsifier having an HLB value in the range from 12 to 18 in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Further particularly preferred antiperspirant compositions according to the invention contain at least one non-ionic oil-in-water emulsifier having an HLB value in the range from 12 to 18, which is selected from linear saturated and unsaturated $C_{12}$-$C_{24}$ alkanols etherified with 7 to 40 ethylene oxide units per molecule, in a total amount from 0.5 to 5 wt. %, preferably 0.8 to 4 wt. %, particularly preferably 1.2 to 3 wt. % and exceptionally preferably 1.5 to 2 wt. %, relative in each case to the total composition. The aforementioned oil-in-water emulsifiers are particularly preferably selected from steareth, ceteth, myristeth, laureth, trideceth, arachideth and beheneth, each having 7-40 ethylene oxide units per molecule, in particular steareth-10, steareth-20, steareth-21, steareth-30, steareth-40, ceteth-10, ceteth-20, ceteth-21, ceteth-30, ceteth-40, laureth-10, laureth-20, laureth-30, trideceth-10, trideceth-20 and trideceth-30, and mixtures thereof.

Further preferred antiperspirant compositions according to the invention contain at least one non-ionic oil-in-water emulsifier having an HLB value in the range from 12 to 18, which is selected from steareth-10, steareth-20, steareth-21, steareth-30, steareth-40, ceteth-10, ceteth-20, ceteth-21, ceteth-30, ceteth-40, laureth-10, laureth-20, laureth-30, trideceth-10, trideceth-20 and trideceth-30 and mixtures thereof, in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Further preferred antiperspirant compositions according to the invention contain at least one cosmetic oil and at least one oil-in-water emulsifier having an HLB value of greater than 7 to 20 and take the form of an oil-in-water emulsion. Within the meaning of the present application the term emulsion does not include microemulsions.

Particularly preferred antiperspirant compositions according to the invention take the form of an oil-in-water emulsion and contain at least one oil-in-water emulsifier having an HLB value of greater than 7 to 20 in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Further particularly preferred antiperspirant compositions according to the invention take the form of an oil-in-water emulsion and contain at least one non-ionic oil-in-water emulsifier having an HLB value in the range from 12 to 18 in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Further particularly preferred antiperspirant compositions according to the invention take the form of an oil-in-water emulsion and contain at least one non-ionic oil-in-water emulsifier having an HLB value in the range from 12 to 18, which is selected from linear saturated and unsaturated $C_{12}$-$C_{24}$ alkanols etherified with 7 to 40 ethylene oxide units per molecule, in a total amount from 0.5 to 5 wt. %, preferably 0.8 to 4 wt. %, particularly preferably 1.2 to 3 wt. % and exceptionally preferably 1.5 to 2 wt. %, relative in each case to the total composition. The aforementioned oil-in-water emulsifiers are particularly preferably selected from steareth, ceteth, myristeth, laureth, trideceth, arachideth and beheneth, each having 7-40 ethylene oxide units per molecule, in particular steareth-10, steareth-20, steareth-21, steareth-30, steareth-40, ceteth-10, ceteth-20, ceteth-21, ceteth-30, ceteth-40, laureth-10, laureth-20, laureth-30, trideceth-10, trideceth-20 and trideceth-30, and mixtures thereof.

Further preferred antiperspirant compositions according to the invention take the form of an oil-in-water emulsion and contain at least one non-ionic oil-in-water emulsifier having an HLB value in the range from 12 to 18, which is selected from steareth-10, steareth-20, steareth-21, steareth-30, steareth-40, ceteth-10, ceteth-20, ceteth-21, ceteth-30, ceteth-40, laureth-10, laureth-20, laureth-30, trideceth-10, trideceth-20 and trideceth-30 and mixtures thereof, in a total amount from 0.5 to 5 wt. %, preferably 0.8 to 4 wt. %, particularly preferably 1.2 to 3 wt. % and exceptionally preferably 1.5 to 2 wt. %, relative in each case to the total composition.

Water-in-Oil Emulsifiers

Further preferred antiperspirant compositions according to the invention contain at least one water-in-oil emulsifier, preferably at least one non-ionic water-in-oil emulsifier, each having an HLB value greater than 1.0 and less than or equal to 7.0, preferably in the range from 3 to 6. Some of these water-in-oil emulsifiers are listed for example in Kirk-Othmer, "Encyclopedia of Chemical Technology", $3^{rd}$ Edition, 1979, Volume 8, page 913. The HLB value can also be calculated for ethoxylated adducts, as already mentioned.

The following are preferred as water-in-oil emulsifiers:

linear or branched, saturated or unsaturated $C_{12}$-$C_{30}$ alkanols, each etherified with 1 to 4 ethylene oxide units per molecule, which are exceptionally preferably selected from steareth, ceteth, myristeth, laureth, trideceth, arachideth and beheneth, each having 1 to 4 ethylene oxide units per molecule, in particular steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 as well as mixtures thereof;

linear saturated alkanols having 12-30 carbon atoms, in particular 16-22 carbon atoms, in particular cetyl alcohol, stearyl alcohol, arachidyl alcohol, behenyl alcohol and lanolin alcohol or mixtures of these alcohols, such as are obtainable by technical hydrogenation of vegetable and animal fatty acids;

esters and in particular partial esters of a polyol having 2-6 C atoms and linear saturated and unsaturated fatty acids having 12-30, in particular 14-22 C atoms, which can be hydroxylated. Such esters or partial esters are for example the mono- and diesters of glycerol or ethylene glycol or the monoesters of propylene glycol with linear saturated and unsaturated $C_{12}$-$C_{30}$ carboxylic acids, which can be hydroxylated, in particular those with palmitic and stearic acid, the sorbitan mono-, di- or triesters of linear saturated and unsaturated $C_{12}$-$C_{30}$ carboxylic acid esters, which can be hydroxylated, in particular those of myristic acid, palmitic acid, stearic acid or of mixtures of these fatty acids, the pentaerythrityl mono-, di-, tri- and tetraesters and the methylglucose mono- and diesters of linear, saturated and unsaturated $C_{12}$-$C_{30}$ carboxylic acids, which can be hydroxylated, of which the mono-, di-, tri- and tetraesters of pentaerythritol with linear saturated fatty acids having 12 to 30, in particular 14 to 22 carbon atoms, which can be hydroxylated, and mixtures thereof are particularly preferred as consistency modifiers and/or water binders. The mono- and diesters are particularly preferred according to the invention. Preferred $C_{12}$-$C_{30}$ fatty acid residues according to the invention are selected from lauric acid, myristic acid, palmitic acid, stearic acid, arachidic acid and behenic acid residues; the stearic acid residue is particularly preferred. Particularly preferred non-ionic water-in-oil emulsifiers according to the invention having an HLB value greater than 1.0 and less than or equal to 7.0 are selected from glyceryl monostearate, glyceryl distearate, glyceryl monopalmitate, glyceryl dipalmitate and mixtures thereof;

sterols, i.e. steroids, which bear a hydroxyl group at the C3 atom of the steroid skeleton and are isolated both from animal tissue (zoosterols, e.g. cholesterol, lanosterol) and from plants (phytosterols, e.g. ergosterol, stigmasterol, sitosterol) and from fungi and yeasts (mycosterols) and can have a low degree of ethoxylation (1-5 EO);

alkanols and carboxylic acids each having 8-24 C atoms, in particular 16-22 C atoms, in the alkyl group and 1 to 4 ethylene oxide units per molecule, which have an HLB value greater than 1.0 and less than or equal to 7.0;

glycerol monoethers of saturated and/or unsaturated, branched and/or unbranched alcohols with a chain length of 8-30, in particular 12-18 carbon atoms;

partial esters of polyglycerols having n=2 to 10 glycerol units and esterified with 1 to 5 saturated or unsaturated, linear or branched, optionally hydroxylated $C_8$-$C_{30}$ fatty acid residues, provided they have an HLB value greater than 1.0 to less than or equal to 7;

and mixtures of the aforementioned substances.

The at least one water-in-oil emulsifier having an HLB value greater than 1.0 and less than or equal to 7.0, preferably in the range from 3 to 6, selected from linear or branched, saturated or unsaturated $C_{12}$ to $C_{30}$ alkanols, each etherified with 1 to 4 ethylene oxide units per molecule, is particularly preferred, exceptionally preferably selected from steareth, ceteth, myristeth, laureth, trideceth, arachideth and beheneth each having 1 to 4 ethylene oxide units per molecule, in particular steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 and mixtures thereof.

It can be preferable according to the invention to use only one water-in-oil emulsifier. In another preferred embodiment the compositions according to the invention contain mixtures, in particular technical mixtures, of at least two water-in-oil emulsifiers.

Preferred compositions according to the invention are characterized in that they contain at least one water-in-oil emulsifier having an HLB value greater than 1.0 and less than or equal to 7.0, preferably in the range from 3 to 6.

Particularly preferred antiperspirant compositions according to the invention contain at least one water-in-oil emulsifier having an HLB value greater than 1.0 and less than or equal to 7.0, preferably in the range from 3 to 6, in a total amount from 1.8 to 3 wt. %, preferably 2 to 2.8 wt. % and particularly preferably 2.4 to 2.6 wt. %, relative in each case to the total weight of the composition according to the invention.

Further preferred antiperspirant compositions according to the invention contain at least one non-ionic water-in-oil emulsifier having an HLB value in the range from 3 to 6, selected from steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 and mixtures thereof, in a total amount from 1.8 to 3 wt. %, preferably 2 to 2.8 wt. % and particularly preferably 2.4 to 2.6 wt. %, relative in each case to the total weight of the composition according to the invention.

Further preferred antiperspirant compositions according to the invention take the form of an oil-in-water emulsion and contain at least one water-in-oil emulsifier having an HLB value greater than 1.0 and less than or equal to 7.0, preferably in the range from 3 to 6, in a total amount from 1.8 to 3 wt. %, preferably 2 to 2.8 wt. % and particularly preferably 2.4 to 2.6 wt. %, relative in each case to the total weight of the composition according to the invention.

Further preferred antiperspirant compositions according to the invention take the form of an oil-in-water emulsion and contain at least one non-ionic water-in-oil emulsifier having an HLB value in the range from 3 to 6, selected from steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 and mixtures thereof, in a total amount from 1.8 to 3 wt. %, preferably 2 to 2.8 wt. % and particularly preferably 2.4 to 2.6 wt. %, relative in each case to the total weight of the composition according to the invention.

Preferred antiperspirant compositions according to the invention contain at least one cosmetic oil, preferably in a total amount from 0.1 to 15 wt. %, particularly preferably 0.3 to 10 wt. %, exceptionally preferably 0.5 to 6 wt. %, relative in each case to the weight of the total antiperspirant composition according to the invention. Such compositions are preferably in the form of an oil-in-water emulsion.

A distinction is made in cosmetic oils between volatile and non-volatile oils. Non-volatile oils are understood to be oils that at 20° C. and under an ambient pressure of 1013 hPa have a vapor pressure of less than 2.66 Pa (0.02 mm Hg). Volatile oils are understood to be oils that at 20° C. and under an ambient pressure of 1013 hPa have a vapor pressure of 2.66 Pa to 40,000 Pa (0.02 mm to 300 mm Hg), preferably 13 to 12,000 Pa (0.1 to 90 mm Hg), particularly preferably 15 to 3000 Pa, exceptionally preferably 30 to 500 Pa.

Particularly preferred non-volatile non-silicone oils according to the invention are selected from the addition products of at least 6 ethylene oxide and/or propylene oxide units with mono- or polyhydric $C_{3\text{-}22}$ alkanols such as butanol, butanediol, myristyl alcohol and stearyl alcohol, for example PPG-13 butyl ether, PPG-14 butyl ether, PPG-9 butyl ether, PPG-10 butanediol, PPG-15 stearyl ether and mixtures thereof.

Particularly preferred compositions according to the invention contain at least one cosmetic oil, selected from PPG-13 butyl ether, PPG-14 butyl ether, PPG-9 butyl ether, PPG-10 butanediol, PPG-15 stearyl ether and mixtures thereof, in a total amount from 0.1 to 15 wt. %, particularly preferably 0.3 to 10 wt. %, exceptionally preferably 0.5 to 6 wt. %, relative to the weight of the total antiperspirant composition according to the invention. Exceptionally preferred compositions according to the invention contain 0.1 to 15 wt. %, particularly preferably 0.3 to 10 wt. %, exceptionally preferably 0.5 to 6 wt. % of PPG-15 stearyl ether, relative in each case to the weight of the total antiperspirant composition according to the invention.

Further particularly preferred non-volatile non-silicone oils according to the invention are esters of linear or branched saturated or unsaturated fatty alcohols having 2 to 30 carbon atoms with linear or branched saturated or unsaturated fatty acids having 2 to 30 carbon atoms, which can be hydroxylated. Esters of linear or branched saturated fatty alcohols having 2 to 5 carbon atoms with linear or branched saturated or unsaturated fatty acids having 10 to 18 carbon atoms, which can be hydroxylated, are preferred. Preferred examples thereof are isopropyl palmitate, isopropyl stearate, isopropyl myristate, 2-hexyldecyl stearate, 2-hexyldecyl laurate, isononyl isononanoate, 2-ethylhexyl palmitate and 2-ethylhexyl stearate. Likewise preferred are isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid 2-butyl octanoate, diisotridecyl acetate, n-hexyl laurate, n-decyl oleate, oleyl oleate, oleyl erucate, erucyl oleate, $C_{12}$-$C_{15}$ alkyl lactate and di-$C_{12}$-$C_{13}$ alkyl malate as well as the benzoic acid esters of linear or branched $C_8$-$C_{22}$ alkanols. Benzoic acid $C_{12}$-$C_{15}$ alkyl esters, available for example as the commercial product Finsolv® TN ($C_{12}$-$C_{15}$ alkyl benzoate), benzoic acid isostearyl esters, available for example as Finsolv® SB, 2-ethylhexyl benzoate, available for example as Finsolv® EB, and benzoic acid 2-octyl dodecyl esters, available for example as Finsolv® BOD, are particularly preferred. Triethyl citrate is a further particularly preferred ester oil.

Further non-volatile non-silicone oils that are preferred according to the invention are selected from branched saturated or unsaturated fatty alcohols having 6 to 30 carbon atoms. These alcohols are frequently also referred to as Guerbet alcohols, as they are obtainable by the Guerbet reaction. Preferred alcohol oils are 2-hexyl decanol, 2-octyl dodecanol and 2-ethylhexyl alcohol. Isostearyl alcohol is likewise preferred. Further preferred non-volatile oils are selected from mixtures of Guerbet alcohols and Guerbet alcohol esters, for example 2-hexyl decanol and 2-hexyl decyl laurate.

The expression "triglyceride" as used below means "glycerol triester". Further non-volatile oils that are preferred according to the invention are selected from the triglycerides of linear or branched, saturated or unsaturated, optionally hydroxylated $C_{8-30}$ fatty acids, provided they are liquid under normal conditions. The use of natural oils, for example soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil and the liquid components of coconut butter and the like, can be particularly suitable. Synthetic triglyceride oils, in particular capric/caprylic triglycerides, for example the commercial products Myritol® 318 or Myritol® 331 (BASF/Cognis) with unbranched fatty acid residues, and also glyceryl triisostearol and glyceryl tri(2-ethylhexanoate) with branched fatty acid residues are particularly preferred. Such triglyceride oils preferably make up a proportion of less than 50 wt. % of the total weight of all cosmetic oils in the composition according to the invention.

Further non-volatile non-silicone oils that are particularly preferred according to the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate and di-(2-hexyldecyl) succinate.

Further non-volatile non-silicone oils that are particularly preferred according to the invention are selected from the addition products of 1 to 5 propylene oxide units with mono- or polyhydric $C_{8-22}$ alkanols such as octanol, decanol, decanediol, lauryl alcohol, myristyl alcohol and stearyl alcohol, preferably from PPG-2 myristyl ether and PPG-3 myristyl ether.

Further non-volatile non-silicone oils that are particularly preferred according to the invention are selected from the symmetrical, asymmetrical or cyclic esters of carbonic acid with $C_6$-$C_{20}$ alcohols, for example di-n-caprylyl carbonate (Cetiol® CC) or di-(2-ethylhexyl)carbonate (Tegosoft DEC). By contrast, esters of carbonic acid with $C_1$-$C_5$ alcohols, for example glycerol carbonate or propylene carbonate, are not compounds that are suitable as the cosmetic oil.

Further oils that can be preferred according to the invention are selected from the esters of dimers of unsaturated $C_{12}$-$C_{22}$ fatty acids (dimer fatty acids) with monohydric linear, branched or cyclic $C_2$-$C_{18}$ alkanols or with polyhydric linear or branched $C_2$-$C_6$ alkanols. The total weight of dimer fatty acid esters is particularly preferably 0.5 to 10 wt. %, preferably 1 to 5 wt. %, relative in each case to the total composition.

Volatile cosmetic oils are conventionally selected from cyclic silicone oils having the INCI name cyclomethicones. The INCI name cyclomethicones is understood to mean in particular cyclotrisiloxane (hexamethyl cyclotrisiloxane), cyclotetrasiloxane (octamethyl cyclotetrasiloxane), cyclopentasiloxane (decamethyl cyclopentasiloxane) and cyclohexasiloxane (dodecamethyl cyclohexasiloxane). These oils have a vapor pressure of approx. 13 to 15 Pa at 20° C.

Cyclomethicones are known in the prior art as being very suitable oils for cosmetic products, in particular for sweat-inhibiting and deodorizing products. Owing to their persistence in the environment, however, it can be preferable according to the invention to avoid the use of cyclomethicones. In an especially preferred embodiment the compositions according to the invention contain 0 to less than 1 wt. % of cyclomethicones, relative to the weight of the composition.

A preferred cyclomethicone substitute is a mixture of $C_{13}$-$C_{16}$ isoparaffins, $C_{12}$-$C_{14}$ isoparaffins and $C_{13}$-$C_{15}$ alkanes, whose viscosity at 25° C. is in the range from 2 to 6 mPas and which have a vapor pressure at 20° C. in the range from 100 to 150 Pa. Such a mixture is obtainable for example under the name SiClone SR-5 from Presperse Inc.

Further preferred volatile silicone oils are selected from volatile linear silicone oils, in particular volatile linear silicone oils having 2 to 10 siloxane units, such as hexamethyldisiloxane ($L_2$), octamethyltrisiloxane ($L_3$), decamethyltetrasiloxane ($L_4$), such as are contained for example in the commercial products DC 2-1184, Dow Corning® 200 (0.65 cSt) and Dow Corning® 200 (1.5 cSt) from Dow Corning, and low-molecular-weight phenyl trimethicone having a vapor pressure at 20° C. of approximately 2000 Pa, such as is obtainable for example from GE Bayer Silicones/Momentive under the name Baysilone Fluid PD 5.

In the interests of a drier skin feel and faster active substance release, preferred antiperspirant compositions according to the invention contain at least one volatile non-silicone oil. Preferred volatile non-silicone oils are selected from $C_8$-$C_{16}$ isoparaffins, in particular from isononane, isodecane, isoundecane, isododecane, isotridecane, isotetradecane, isopentadecane and isohexadecane, as well as mixtures thereof. $C_{10}$-$C_{13}$ isoparaffin mixtures are preferred, in particular those having a vapor pressure at 20° C. of 10 to 400 Pa, preferably 13 to 100 Pa.

Further preferred antiperspirant compositions according to the invention in the form of oil-in-water emulsions are characterized in that the at least one propylene glycol monoester of branched saturated $C_6$-$C_{30}$ alkane carboxylic acids is selected from propylene glycol monoisostearate, propylene glycol monoisopalmitate, propylene glycol monoisobehenate, propylene glycol monoisoarachinate, propylene glycol monoisomyristate, propylene glycol monoisocaprate, propylene glycol monoisocaprinate and propylene glycol monoisocaprylate and mixtures thereof. Further preferred antiperspirant compositions according to the invention in the form of oil-in-water emulsions are characterized in that the at least one branched saturated $C_{10}$-$C_{30}$ alkanol is selected from isostearyl alcohol, isocetyl alcohol, isomyristyl alcohol, isotridecyl alcohol, isoarachidyl alcohol, isobehenyl alcohol, isocapryl alcohol, isocaprinyl alcohol, isocaprylyl alcohol and mixtures thereof.

Further preferred antiperspirant compositions according to the invention in the form of oil-in-water emulsions are characterized in that at least one non-ionic emulsifier having an HLB value in the range from 3 to 6 and at least one non-ionic emulsifier having an HLB value in the range from 12 to 18 are contained.

Further preferred antiperspirant compositions according to the invention in the form of oil-in-water emulsions are characterized in that at least one non-ionic emulsifier having an HLB value in the range from 3 to 6 in a total amount from 1.8 to 3 wt. % and at least one non-ionic emulsifier having an HLB value in the range from 12 to 18 in a total amount from 1 to 2 wt. % are contained, the stated amounts relating in each case to the total weight of the composition according to the invention.

Further preferred antiperspirant compositions according to the invention in the form of oil-in-water emulsions are characterized in that steareth-2 is contained as the non-ionic emulsifier having an HLB value in the range from 3 to 6 and at the same time steareth-21 as the non-ionic emulsifier having an HLB value in the range from 12 to 18.

Further preferred antiperspirant compositions according to the invention in the form of oil-in-water emulsions are characterized in that steareth-2, steareth-21 and PPG-15 stearyl ether are contained.

Further preferred antiperspirant compositions according to the invention contain in total at most 3 wt. %, preferably at most 1 wt. % and particularly preferably 0 wt. %, relative in each case to the total weight of the composition according to the invention, of monohydric $C_1$-$C_3$ alkanols, such as ethanol or isopropanol.

Most particularly preferred compositions according to the invention are characterized in that they contain at least one cosmetic oil and at least one oil-in-water emulsifier having an HLB value of greater than 7 to 20 and take the form of an oil-in-water emulsion which is not a microemulsion.

In addition to the aforementioned ingredients, the compositions according to the invention can contain further additives and auxiliary substances, which for example improve their storage life, such as preservatives, for example phenoxyethanol, methylparaben or propylparaben, antioxidants, for example tetradibutyl pentaerythrityl hydroxyhydrocinnamates, lipochroman-6, tocopherol, tocopheryl acetate or ascorbic acid and derivatives thereof, vitamins and derivatives thereof, such as tocopherol, tocopheryl acetate, ascorbic acid, panthenol or pantolactone, perfumes, essential oils, menthol and menthol derivatives having a skin-cooling effect, care substances having a skin-calming effect, such as bisabolol and allantoin, active agents which delay hair growth, for example eflornithine or glycyrrhizin and derivatives thereof, moisturizers and humectants, such as 1,2-propylene glycol, glycerol, 2-methyl-1,3-propanediol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols, such as 1,2,6-hexanetriol, 1,2-octanediol, 1,8-octanediol, dipropylene glycol, tripropylene glycol, diglycerol, triglycerol, erythritol, sorbitol, cis-1,4-dimethylol cyclohexane, trans-1,4-dimethylol cyclohexane, any isomer blends of cis- and trans-1,4-dimethylol cyclohexane, urea, N,N'-bis-(2-hydroxyethyl) urea, sodium pyrrolidone carboxylate, plant extracts, for example aloe vera extract, natural fats and oils, such as jojoba oil, evening primrose oil or linseed oil, saturated and unsaturated fatty acids, such as stearic acid, oleic acid, linoleic acid, linolenic acid or gamma-linolenic acid, squalane, squalene, deodorant active agents, such as silver salts, colloidal silver, zeolites, 2-benzylheptan-1-ol, anisic alcohol, mixtures of 2-benzylheptan-1-ol and phenoxyethanol, 3-(2-ethylhexyloxy)-1,2-propanediol or tropolone, and mixtures of these substances.

The embodiment examples below are intended to clarify the subject matter of the present invention without restricting its scope thereto.

EXAMPLES

Intelimer® 13-1 (Air Products) was used as the partially crystalline polymer having $C_8$-$C_{30}$ alkyl side chains. This polymer (melting point 48° C.) was mixed in the specified weight ratios with perfume oil or skin-cooling active agent, melted and then processed into particles having a number-average particle size of 10 to 30 μm.

All values are given in wt. % (wt/wt).

Particle 1
Intelimer IPA 13-1 polymer/perfume oil 1.0/0.5 (wt/wt)
Melting range 29-31° C.

Particle 2
Intelimer IPA 13-1 polymer/menthyl lactate 1.0/0.5 (wt/wt)
Melting range 33-35° C.

Particle 3
Intelimer IPA 13-1 polymer/menthyl acetate 1.0/0.5 (wt/wt)
Melting point 27° C.

Particle 4
Performa V 343 polymer/perfume oil 1.0/0.5 (wt/wt)
Melting range 24-27° C.

Particle 5
Performa V 343 polymer/menthyl lactate 1.0/0.5 (wt/wt)
Melting range 29-34° C.

Particle 6
Performa V 343 polymer/menthyl acetate 1.0/0.25 (wt/wt)
Melting range 27-30° C.

The particles according to the invention were used to produce the following compositions according to the invention:

|  | 1 wt. % | 2 wt. % | 3 wt. % | 4 wt. % | 5 wt. % | 6 wt. % |
|---|---|---|---|---|---|---|
| Aluminum chlorohydrate | 20.0 | 20.0 | 20.0 | 20.0 | 20.0 | 20.0 |
| Steareth-21 | 1.5 | 1.5 | 1.5 | 1.5 | 1.5 | 1.5 |
| Steareth-2 | 2.4 | 2.4 | 2.4 | 2.4 | 2.4 | 2.4 |
| PPG-15 stearyl ether | 0.5 | 0.5 | 0.5 | 0.5 | 0.5 | 0.5 |
| Aluminum starch octenylsuccinate | 0.1 | 0.1 | 0.1 | 0.1 | 0.1 | 0.1 |
| Propylene glycol | 0.5 | 0.5 | 0.5 | 0.5 | 0.5 | 0.5 |
| EDTA | 0.1 | 0.1 | 0.1 | 0.1 | 0.1 | 0.1 |
| Dehydroxanthan gum | 0.1 | 0.1 | 0.1 | 0.1 | 0.1 | 0.1 |
| Hydroxyethyl cellulose | 0.1 | 0.1 | 0.1 | 0.1 | 0.1 | 0.1 |
| Complex 1 | 0.25 | — | — | — | — | — |
| Complex 2 | — | 0.5 | — | — | — | — |
| Complex 3 | — | — | 0.1 | — | — | — |
| Complex 4 | — | — | — | 0.25 | — | — |
| Complex 5 | — | — | — | — | 0.5 | — |
| Complex 6 | — | — | — | — | — | 0.2 |
| Water | to 100 | to 100 | to 100 | to 100 | to 100 | to 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A deodorant cosmetic composition, comprising:
    water; and
    0.01 to 10 wt. % based on the weight of the cosmetic composition of one or more particles said one or more particles comprising, relative in each case to the particle weight,
        30 to 90 wt. % of polyalphaolefin wax(es) and
        10 to 70 wt. % of one or more cosmetic active agents selected from the group consisting of fragrances, cooling active agents, and mixtures of fragrances and cooling active agents
    wherein the one or more particles has a melting point of 23 to 40° C. as measured in accordance with ASTM D 36.

2. The deodorant cosmetic composition according to claim 1, further comprising at least one antiperspirant active agent.

3. The deodorant cosmetic composition according to claim 1, further comprising at least one deodorant active agent.

4. The deodorant cosmetic composition according to claim 1, wherein the composition is an antiperspirant composition and includes at least one oil-in-water emulsifier having an HLB value of greater than 7 to 20 in a total amount from 0.5 to 5 wt. %.

5. The deodorant cosmetic composition according to claim 1, wherein the composition is an antiperspirant composition and further includes at least one non-ionic oil-in-water emulsifier having an HLB value of 12 to 18 and is present in an amount of 0.5 to 5 wt. % based on the total weight of the composition.

6. The deodorant cosmetic composition according to claim 1, wherein the composition is an antiperspirant composition and includes at least one non-ionic oil-in-water emulsifier having an HLB value of 12 to 18 which is selected from linear saturated and unsaturated $C_{12}$-$C_{24}$ alkanols etherified with 7 to 40 ethylene oxide units per molecule, the non-ionic oil-in-water emulsifier present in an amount of 0.5 to 5 wt. % based on the total weight of the composition.

7. The deodorant cosmetic composition according to claim 1, wherein the composition is an antiperspirant composition and includes 1.8 to 3 wt % of at least one non-ionic water-in-oil emulsifier having an HLB value of 3 to 6 and being selected from the group consisting of steareth-2, steareth-3, steareth-4, ceteth-2, ceteth-3, ceteth-4, myristeth-2, myristeth-3, myristeth-4, laureth-2, laureth-3, laureth-4, trideceth-2, trideceth-3 and trideceth-4 and mixtures thereof.

8. The deodorant cosmetic composition according to claim 1, wherein the composition further comprises 0.05 wt % to 1 wt % of at least one non-ionic thickening polymer selected from the group consisting of cellulose and cellulose ethers and mixtures thereof.

9. The deodorant cosmetic composition according to claim 1, wherein the composition further comprises 0.05 to 1 wt % of dehydroxanthan gum based on the total weight on the composition.

10. The deodorant cosmetic composition according to claim 1, wherein, based on the total weight of the composition, the composition further comprises 0.05 to 1.0 wt % of dehydroxanthan gum and 0.05 to 1 wt. % of hydroxyethyl cellulose.

11. The deodorant cosmetic composition according to claim 1, wherein the particle has a number average particle diameter of 500 nm to 50 µm.

12. The deodorant cosmetic composition according to claim 1, wherein the at least one polyalphaolefin wax has a melting point of 30 to 75° C. measured in accordance with ASTM D 36.

13. The deodorant cosmetic composition according to claim 1, wherein the at least one polyalphaolefin wax has a melting point of 40 to 55° C. measured in accordance with ASTM D 36.

14. The particle according to one of claim 1, wherein the at least one polyalphaolefin wax(es) comprises 50 to 75 wt. % of the particle weight and the at least one cosmetic active agent comprises 25 to 50 wt. % of the particle weight.

15. The deodorant cosmetic composition according to claim 1, wherein the particle has a melting point of 27 to 32° C. as measured in accordance with ASTM D 36.

* * * * *